(12) United States Patent
Behnk et al.

(10) Patent No.: US 9,156,630 B2
(45) Date of Patent: Oct. 13, 2015

(54) SAMPLE RACK HANDLING UNIT

(71) Applicant: Roche Diagnostics Operations, Inc., Indianapolis, IN (US)

(72) Inventors: Holger Behnk, Hamburg (DE); Joerg Burmester, Horgen (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 129 days.

(21) Appl. No.: 13/742,479

(22) Filed: Jan. 16, 2013

(65) Prior Publication Data

US 2013/0195720 A1    Aug. 1, 2013

(30) Foreign Application Priority Data

Jan. 30, 2012 (EP) .................................... 12153043

(51) Int. Cl.
*G01N 35/04* (2006.01)
*G01N 35/02* (2006.01)
*B65G 49/00* (2006.01)
*B01L 9/00* (2006.01)

(52) U.S. Cl.
CPC ............. *B65G 49/00* (2013.01); *G01N 35/026* (2013.01); *G01N 35/04* (2013.01); *B01L 2200/025* (2013.01); *G01N 2035/0415* (2013.01); *G01N 2035/0429* (2013.01); *G01N 2035/0465* (2013.01)

(58) Field of Classification Search
None
See application file for complete search history.

(56) References Cited

U.S. PATENT DOCUMENTS

| | | | |
|---|---|---|---|
| 4,022,579 | A | 5/1977 | Revillet et al. |
| 5,351,801 | A | 10/1994 | Markin et al. |
| 5,941,366 | A | 8/1999 | Quinlan et al. |
| 6,426,044 | B1 | 7/2002 | Cohen et al. |
| 2003/0129095 | A1 | 7/2003 | Farina et al. |
| 2010/0028124 | A1 | 2/2010 | Lackner et al. |
| 2010/0028203 | A1 | 2/2010 | Frey et al. |
| 2010/0166606 | A1 | 7/2010 | Koike et al. |
| 2011/0250091 | A1 | 10/2011 | Kaiga |

FOREIGN PATENT DOCUMENTS

EP    0632271 A1    1/1995

*Primary Examiner* — Neil N Turk
(74) *Attorney, Agent, or Firm* — Roche Diagnostics Operations, Inc.

(57) ABSTRACT

A sample rack handling unit comprising an onload section for loading sample racks holding a sample container is presented. The onload section comprises an onload edge and a receiving area with an onload rail longitudinally on the receiving area parallel to the onload edge. The onload rail engages a recess on the rack bottom such that the rack longitudinally slides on the receiving area along the onload rail when the rack is engaged. The onload rail has a base portion and a protrusion extending from the base portion. The protrusion faces the onload edge and the base portion comprises an inclined onload rail side opposite the onload edge such that the recess engages the onload rail when the rack is loaded on the receiving area from the onload edge transversely to the onload rail and the recess disengages the onload rail by sliding the rack towards the onload edge.

14 Claims, 10 Drawing Sheets

SAMPLE RACK HANDLING UNIT

CROSS-REFERENCE TO RELATED APPLICATIONS

This application is a continuation of EP 12153043.0, filed Jan. 30, 2012, which is hereby incorporated by reference.

BACKGROUND

The present disclosure generally relates to a sample rack handling unit and, in particular, to a sample rack handling unit comprising a rack onload section for loading one or more sample racks. It also relates to an analytical instrument comprising such a sample rack handling unit and to a method of handling sample racks.

Different types of sample handling units have been developed for various analytical instruments. Such sample handling units are used to load sample racks holding sample containers, such as sample tubes containing analytical samples to be analyzed, into an instrument and for taking the racks out of the instrument after having been analyzed. Several sample handling units comprise an onload section wherein sample racks are queued before entering into a processing section. In the processing section, operations are performed with the sample tubes such as aspiration of sample from the sample tubes. Sample racks are then transported further to an offload section wherein sample racks are queued before being taken out from the sample handling unit.

There are systems, which comprise buffer sections and enable random access to the racks and/or sample tubes in the racks contained in such a buffer. Others comprise robotic arms and grippers to pick and transport sample racks between different sections. Some comprise a dedicated onload section for sample racks holding sample tubes with urgent samples having priority in the queue. Such systems are however large, bulky, complex and expensive, therefore suitable only for larger high-throughput instruments. Smaller instruments and/or instruments with smaller throughput normally integrate simpler and more compact sample rack handling units. These typically comprise a single and linear transportation path. This means that if a sample has to be re-analyzed or if a sample with higher priority has to be analyzed, the rack containing that sample will be queued after all the others, which are already in the transportation path, therefore causing a significant delay in testing and retesting. Also, sample racks are typically engaged with a rail, for example, via a recess at the bottom of the racks as shown in FIG. 2b, such as to be able to follow the transportation path in a controlled manner, for example, without falling over or getting jammed. This constrain limits further the flexibility of such systems in handling sample racks.

Therefore, there is a need for a compact, simple and inexpensive sample rack handling unit that offers more flexibility and ease of use by comprising a rack onload section having an onload rail that enables a sideway engagement with a rack from a rack onload edge and a sideway disengagement by sliding the rack on an inclined onload rail side in the direction of the rack onload edge. In this way, it can be possible to load a rack or a plurality of racks at any position along the transportation path in the rack onload section, as well as to change the position of one or more racks or to remove one or more racks from any position, if for example, it is desired to replace a rack with another rack. At the same time, it can ensured that the racks can be smoothly transported longitudinally along the rail. Moreover, the shape and arrangement of the rail can allow an easy and ergonomic handling of the racks for a smooth and quick manual or automated operation both when engaging and when disengaging a rack.

SUMMARY

According to the present disclosure, a sample rack handling unit is presented. The sample rack handling unit comprises a rack onload section for loading one or more sample racks to hold at least one sample container. The rack onload section comprises a rack onload edge and a rack receiving area with an onload rail longitudinally arranged on the rack receiving area parallel to the rack onload edge. The onload rail engages a recess located at the bottom of a rack such that the rack is longitudinally slidable on the rack receiving area along the onload rail when the rack is engaged. The onload rail has a cross-section comprising a wedged or substantially triangular base portion and a protrusion extending from the base portion. The protrusion faces the rack onload edge and the base portion comprises an inclined onload rail side arranged opposite to the rack onload edge such that the recess engages the onload rail when the rack is loaded on the rack receiving area from the rack onload edge in a direction transverse to the onload rail and the recess disengages from the onload rail by sliding the rack in the direction of the rack onload edge.

Accordingly, it is a feature of the embodiments of the present disclosure to provide a compact, simple and inexpensive sample rack handling unit that offers more flexibility and ease of use. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A "sample rack handling unit" can be a work cell either integrated into an instrument or removably coupled to an instrument and can act as an interface between the user and the instrument for loading and unloading sample racks holding at least one sample container containing at least one sample to be processed by the instrument.

An "instrument" can be either a stand-alone apparatus, or a module within a larger apparatus, assisting users with the detection, for example, qualitative and/or quantitative evaluation of samples for diagnostic purpose, or with the sorting and/or preparation of samples before detection, or with the storing and/or disposal of samples after detection. In particular, the instrument may be related to analytical and/or to pre-analytical and/or to post-analytical sample processing steps.

A "sample container" can be either a sample collection test tube, also called "primary tube", which can be used to receive a sample such as a blood sample from a patient and to transport the sample contained therein to an analytical laboratory for diagnostics purposes, or a "secondary vessel", which may be used to receive an aliquot of sample from a primary tube. A primary sample tube is typically made of glass or plastics, may have different sizes, can have a closed end and an open end closed by a closure, which may be of different materials, can assume different shapes and colors. Sample tubes may be loaded in the sample rack handling unit with or without closure. The instrument may, for example, comprise a decapping device to remove closures from the sample tubes or it may aspirate samples from the sample tubes through the closures. Secondary vessels are typically smaller and may also be provided with or without closure. "Samples" are typically liquid biological samples, in which one or more analytes of diagnostic interest can be potentially found, such as body fluids like blood, serum, plasma, urine, milk, saliva, cerebrospinal fluid, and the like.

A "sample rack" can be a carrier, typically made of plastics and/or metal, adapted for receiving, holding and transporting one or more sample containers. The sample rack handling unit can be particularly suitable for sample racks carrying a plurality of sample containers, for example, up to five or more sample containers, for example, disposed in one or more rows. The sample rack can typically comprise two shorter sidewalls, defining the width of the rack, and two longer longitudinal sidewalls, defining the length of the rack. The rack can comprise a bottom and a top side, defining the height of the rack, the top side comprising a plurality of cavities linearly arranged over the length of the rack to receive a corresponding number of sample containers. Apertures, windows or slits may be present on at least one longer side to enable visual or optical inspection or reading of the sample containers or of the samples in the sample containers or of a label, such as a barcode, present on the sample containers held in the sample rack. The bottom side can comprise a recess having a width equal to the width of the rack such as to extend through the entire width of the rack and a length shorter than the length of the rack, and can be typically substantially shaped as a T or inverted L, that is having a narrower lower section and a larger upper section extending with one or two recess arms towards one or both shorter sides of the rack respectively. The rack can typically have an asymmetric geometry allowing the rack to be loaded and/or transported only in one orientation. The asymmetric geometry may be achieved for example by different geometries of the sides, for example, of the shorter sides, wherein one side may be for example, flat and the other beveled. Also or alternatively, the recess at the bottom may be in a position different from the center of the rack, that is, closer to one side.

The sample rack handling unit can comprise at least a rack onload section. A "rack onload section" can be an integrated, or separable, component of the rack handling unit to load and possibly unload one or more racks. The rack onload section can comprise a rack onload edge and a rack receiving area with an onload rail longitudinally arranged on the rack receiving area substantially parallel to the rack onload edge. The rack receiving area can typically be substantially flat and can have a width to accommodate the length of a rack and can have a length to accommodate a plurality of racks arranged with their respective longer sides substantially parallel to each other side by side and with substantially the same orientation. The rack receiving area can be delimited at one side by the "rack onload edge," which can be a border of the rack receiving area typically facing the outside of the instrument at a location accessible from the outside by the user. The onload rail can be substantially parallel to the onload edge and according to one embodiment it can be outside of the center of the rack receiving area so that it can engage with the recess located at the bottom of a rack and the rack can longitudinally slide on the rack receiving area along the onload rail only when the rack is in one orientation.

The term "longitudinally" can indicate a direction substantially parallel to the onload rail and, in general, to the transportation path, wherein a rack engaged with the onload rail can be oriented such that the sides of the rack comprising the recess, typically the longer sides, can be substantially orthogonal to the onload rail.

The onload rail can comprise a base portion having a wedged, or substantially triangular, cross-section and a protrusion extending from the base portion. The protrusion can face the rack onload edge and the base portion can have an inclined onload rail side opposite the rack onload edge. The protrusion can be a ridge extending outwards from the upper corner of the wedge in the direction of the rack onload edge and can have a shape that can engage with the recess on the bottom of a rack. The protrusion can extend longitudinally along the onload rail and can have a length allowing a plurality of racks to engage with their respective recesses side by side. The shape of the protrusion can be substantially complementary to the shape of a recess arm in the upper section of the recess. The onload rail can thus only be in part form-fit, that is form-fit only from one side with the recess of a rack, wherein "form-fit" can mean substantially complementary such that one shape can fit in the other with a tolerance which can enable smooth sliding.

The term "engaged" can therefore mean that due to the form-fit part when the recess and the onload rail can be engaged, the bottom of the rack can lay on the rack receiving area and can slide longitudinally along the onload rail but can be prevented from disengaging by lifting the rack vertically or by sliding the rack in a direction opposite to the onload edge. Due to the non-form-fit part, the rack can however be disengaged by sliding the rack in the direction of the onload edge on the inclined onload rail side. Of course, a rack may disengage also by sliding longitudinally to one extremity of the onload rail.

The inclined onload rail side may extend longitudinally for a length equivalent to the length of the protrusion and may have a flat, or curved, surface between the upper corner of the wedge and the rack receiving area. The inclined onload rail side can have a slope, or radius, that can enable the recess of a rack engaged with the protrusion when the rack is loaded on the rack receiving area from the rack onload edge in a direction transverse to onload rail and can enable the recess to be disengaged from the onload rail by sliding the rack on the inclined onload rail side in the direction of the rack onload edge.

According to one embodiment, the rack onload edge can comprise an inclined onload edge side facing the onload rail and substantially parallel to the inclined onload rail side such that the recess can engage with the onload rail and can disengage from the onload rail by sliding the rack transversally on the inclined onload rail side and the inclined onload edge side in opposite directions respectively. The onload rail and the onload edge may have the same, or similar, height so that the bottom of the rack may be laid substantially horizontal as a bridge on top of the onload rail and onload edge. The distance between the onload edge and the onload rail can be substantially equivalent to the distance between the recess and one shorter side of the rack so that by sliding the rack in one orientation from the onload edge towards the onload rail the bottom of the rack can be gradually lowered until the recess engages with the protrusion of the onload rail and the bottom of the rack lays flat on the rack receiving area Analogously, by sliding the rack in the opposite direction towards the onload edge the rack can gradually be raised until the recess disengages and the bottom of the rack lays substantially flat on top of the onload rail and onload edge. Loading and unloading thereby can further be facilitated as only a smooth and linear movement may be required to accomplish engagement and disengagement, which can be without particular handling or tilting of the rack. This can enable moreover to easily load and/or unload a plurality of racks at the same time with the same easy movement. It can also enable the loading and/or the unloading to be more easily automated.

The term "transverse" or "transversally" can therefore be used to indicate a direction substantially orthogonal to the onload rail and in general to the transportation path. In the transverse movement, the rack can be oriented such that the sides of the rack comprising the recess, typically the longer sides, can be substantially parallel to the direction of movement.

According to one embodiment, the rack handling unit can comprise a sample processing section to receive racks from the rack onload section and to enable processing of samples from sample containers contained in the racks. The sample processing section can comprise a rack processing area and a processing rail on the rack processing area, the processing rail can engage the recess such that the rack can longitudinally slide on the rack processing area along the processing rail when the rack is engaged.

According to one embodiment, the processing rail can have a cross-section, which can be form-fit with the recess of the rack, for example, comprising at least two protrusions such that the recess can engage and disengage only by sliding a rack on the rack processing area longitudinally along the processing rail, for example engaged at one extremity of the processing rail and disengaged at the other extremity of the processing rail after sliding along the all length of the processing rail. This can mean that a rack can be prevented from being disengaged transversally or in the upward direction from the processing rail and can therefore also be prevented from rising with the bottom from the rack processing area.

"Processing" can mean performing operations related to the use of samples for qualitative and/or quantitative evaluation for diagnostic purpose. Processing may comprise operations such as pipetting, that is aspirating and or dispensing, dosing, diluting, mixing of samples and/or samples with reagents. Processing may comprise removing closures from sample containers or piercing closures. The sample processing section may comprise a pipetting unit or may be adapted to cooperate with a pipetting unit adapted to pipette at least one sample from at least one sample container.

According to one embodiment, the sample processing section can comprise a rack holding mechanism that can move between at least an open position and a holding position. In the holding position, the rack holding mechanism can prevent one or more racks from moving longitudinally along the processing rail. The holding mechanism can assume the holding position during processing and the open position when one or more racks may be moved forward along the transportation path. According to one embodiment, the pipetting unit can pipette at least one sample from at least one sample container when the holding mechanism is in the holding position. In other words, the holding mechanism can be in the holding position when a pipetting step is required.

The holding mechanism may be, for example, a ridge at one edge of the rack processing area substantially parallel to the processing rail, which in the open position can be retracted and in the holding position can be advanced such as to come into contact with one or more racks on the rack processing area. The holding mechanism may apply a frictional force on one shorter side of one or more racks engaged with the processing rail, such as to prevent them from moving longitudinally along the processing rail. According to one embodiment, the holding mechanism can have a front comb-like shape comprising a plurality of protruding teeth embracing a respective number of beveled shorter sides of a plurality of racks in the holding position. This can be another way to prevent the racks from moving longitudinally along the processing rail during processing.

According to one embodiment, the sample rack handling unit can comprise a sample rack offload section to receive racks from the sample processing section. A "sample rack offload section" can be an integrated, or separable, component of the rack handling unit to unload one or more racks. The rack offload section can comprise an offload rack area and an offload rail on the offload rack area. According to one embodiment, the offload rail can have a wedged, or substantially triangular, cross-section similar to that of the onload rail. The offload rail can comprise a protrusion and an inclined offload rail side such that the recess can disengage from the offload rail by sliding the rack transversally on the inclined offload rail side or by sliding the rack longitudinally along the offload rail. In this way, it can be possible, for example, to unload a rack from the rack offload area at any position along the offload rail and re-load it, for example, for re-testing, on the rack receiving area of the rack onload section, for example, at a priority position along the onload rail before other racks already present on the rack receiving area The rack offload section may comprise a rack offload edge similar to the rack onload edge of the rack onload section.

According to one embodiment, the sample rack offload section can be translatable and/or removable from the sample rack handling unit. The sample rack offload section may be for example a translatable drawer for easier access to the racks on the rack offload area. Also or alternatively, the rack offload section may be a removable tray, for example, comprising a transportation handle for being hand held and removed from the rack handling unit with one or more racks on the rack offload area.

According to one embodiment, the sample rack offload section can comprise a separate rack offload tray to receive racks from the rack offload area comprising a transportation handle for being hand held, a rack tray area and a tray rail on the rack tray area alignable with the offload rail. In this way, one or more racks can be transferred from the rack offload area to the rack tray area by sliding the racks along the offload rail in direction of the tray rail so that the racks can disengage from the offload rail and can engage with the tray rail when the offload rail and the tray rail are aligned. Also, the tray rail can have a wedged, or substantially triangular, cross-section similar to that of the offload rail. The tray rail can comprise a protrusion and an inclined tray rail side such that the recess of the rack can be disengaged from the tray rail by sliding the rack transversally on the inclined offload rail side. Alternatively, the racks may be unloaded from the offload tray by sliding the racks longitudinally along the tray rail. The rack offload tray may thus be conveniently used to unload with one sliding movement a plurality of racks from the rack offload section.

According to one embodiment, the rack onload section, the sample processing section and the rack offload section can be arranged such that at least two rack rails chosen from the group of the onload rail, the processing rail and the offload rail can be aligned with each other such that the racks can slide between the rack rails.

According to one embodiment, the sample processing section and the rack offload section can be arranged such that the processing rail and the offload rail can be aligned with each other such that the racks can slide from the processing rail to the offload rail. According to one embodiment, the rack onload section can be substantially parallel and adjacent to the sample processing section and the rack offload section. This arrangement may confer more compactness to the sampler rack handling unit, wherein the rack onload section may be longer than the sample processing section or the rack offload section, for example, as long as the sum of the length of the sample processing section and the rack offload section so that a larger number of racks may be loaded on the rack receiving area.

According to one embodiment, the sample rack handling unit can comprise at least one push or pull element translatable in a direction parallel to at least one rack rail chosen from the group of the onload rail and the processing rail such as to push or pull one or more sample racks engaged with the onload rail and/or with the processing rail longitudinally along the onload rail and/or processing rail.

According to one embodiment, the rack onload section can comprise at least one onload push element for pushing one or more racks on the rack onload area longitudinally along the onload rail and the sample processing section can comprise at least one processing push element for pushing one or more racks on the rack processing area longitudinally along the processing rail.

According to one embodiment, the at least one push or pull element can push or pull only in one direction and can be retractable when translated in the opposite direction. The onload push element may push in the direction of the sample processing section along the transportation path and can retract in the opposite direction, for example, to return to a previous position before pushing again, for example, for re-compacting a plurality of racks spread on the rack receiving area along the onload rail, for example, after leaving a gap between racks due to the transversally unloading of a rack. Analogously, the processing push element may push only in the direction of the rack offload section and may retract when translated in the opposite direction.

According to one embodiment, at least the rack receiving area and/or the rack processing area can comprise at least one slit arranged parallel to the onload rail and/or the processing rail such that the at least one push element can be translated through the at least one slit.

According to one embodiment, the rack receiving area can comprise two slits, one slit on either side of the onload rail and an onload push element for each slit.

According to one embodiment, the rack processing area can comprise two slits, one slit on either side of the processing rail and a processing push element for each slit.

The at least one push or pull element may be for example pivotally coupled to one or more spindle drives driven by one or more electric motors, located for example under the rack onload section and/or under the sample processing section. The at least one push or pull element may comprise a resilient member such as a spring for passively switching the push or pull element between a pushing or pull mode and a retraction mode. For example, the onload push element or elements may emerge from underneath the rack receiving area above the rack receiving area through the slit or slits and be pivotally mounted such as to apply a push force on the longer side of the first encountered rack. By moving the first rack forwards, any other rack located downstream can also be pushed when it comes in contact with the preceding rack. On the contrary, when the onload push element is translated in the opposite direction, for example, to re-start pushing from the beginning of the rack receiving area or for re-compacting racks spread along the onload rail, it can retract if a rack is encountered on its way. It can thus retreat below the bottom of the rack rather than pushing the rack backwards and can re-emerge after passing on the other side of the rack.

According to one embodiment, the sample rack handling unit can comprise a sample rack transfer section located between the rack onload section and the sample processing section along the transportation path, the rack transfer section comprising a transfer element to transfer at least one rack at a time from the rack onload section to the sample processing section. The rack transfer element may push a rack in a direction orthogonal to the rack onload rail along a transfer area after the rack has disengaged from the onload rail. The transfer element may be for example a horizontal bar, rod or the like to fit in the recess of the rack. The onload push element and the transfer element may cooperate such that the recess can disengage from the onload rail and can engage with the transfer element aligned with the onload rail. The transfer element can then push the rack on the transfer area until the transfer element and the recess are aligned with the processing rail of the sample processing section. The processing push element may then push or pull the rack onto the rack processing area so that the recess can engage the processing rail.

According to one embodiment, the sample rack transfer section can comprise an identification sensor, such as a barcode reader, an RFID reader or an optical detector such as a camera. In this way, each rack and/or the sample containers in the rack may be identified before being transferred to the sample processing section, for example, by reading the information contained for example in a barcode or RFID chip attached on one side of the rack and/or of the sample container.

An analytical instrument for the in vitro diagnostic analysis of biological samples can comprise a sample handling unit according to any of the above embodiments and at least one analytical unit for analyzing at least one sample from the at least one sample container held in the at least one sample rack. Examples of analytical instruments can be clinical chemistry analyzers, coagulation chemistry analyzers, immunochemistry analyzers, urine analyzers, used to detect the result of chemical or biological reactions or to monitor the progress of chemical or biological reactions via one or more detectors and detecting methods. An analytical instrument may comprise units assisting with the pipetting, dosing, mixing of samples and/or reagents. The analytical instrument may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a reaction vessel or cuvette feeding unit. It may comprise one or more liquid processing units, such as a pipetting unit, to deliver samples and/or reagents to the reaction vessels. The pipetting unit may comprise a reusable washable needle, for example, a steel needle, or disposable pipette tips. The analytical instrument may further comprise one or more mixing units, comprising for example a shaker to shake a cuvette comprising a liquid or a mixing paddle to mix liquids in a cuvette or reagent container.

Figure 1A:
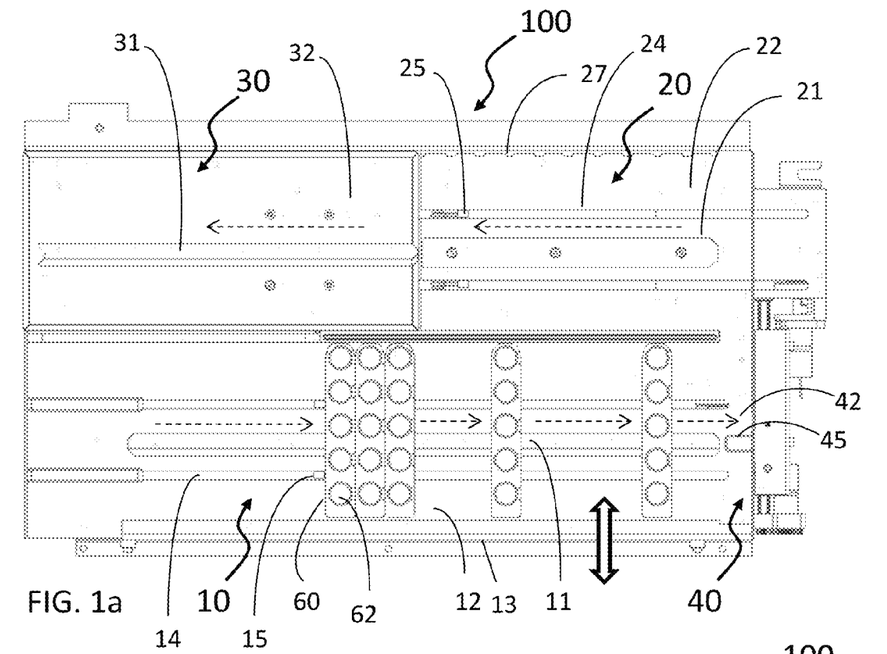
FIGS. 1a-b illustrate schematically an example of sample rack handling unit seen from the top and in perspective according to an embodiment of the present disclosure.
Figure 1B:
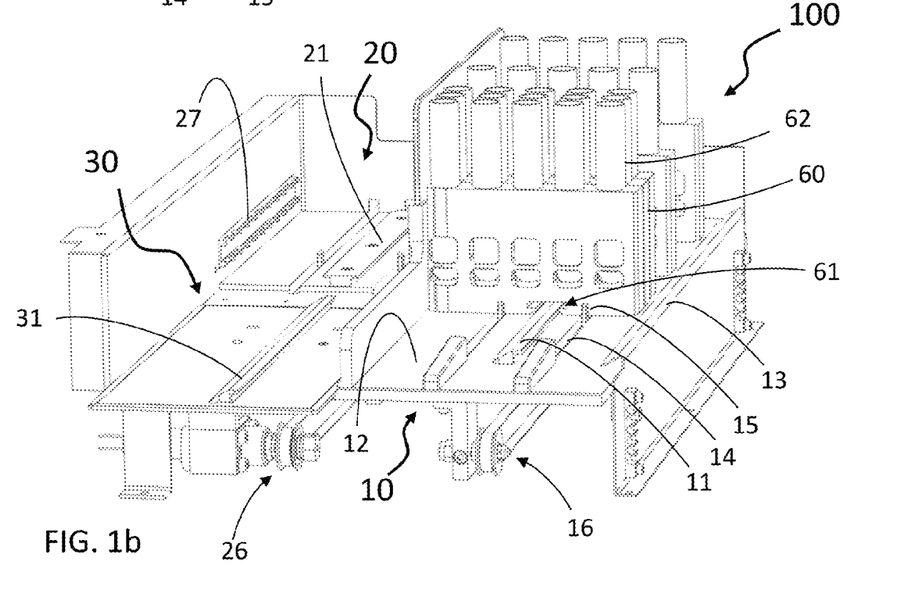

Referring initially to FIG. 1, an example of sample rack handling unit 100 is shown. In particular, FIG. 1a shows a top view and FIG. 1b shows a perspective view of the sample rack handling unit 100. The sample rack handling unit 100 can comprise a sample rack onload section 10 for loading a plurality of sample racks 60, holding a plurality of sample tubes 62 (shown without closure). The sample rack handling unit 100 can further comprise a sample processing section 20, a sample rack offload section 30 and a sample rack transfer section 40 to transfer racks 60 between the sample rack onload section 10 and the sample processing section 20. The sample processing section 20 and the rack offload section 30 can be substantially parallel and adjacent to the onload section 10. The onload section 10 can comprise a rack onload edge 13 and a rack receiving area 12 with an onload rail 11 longitudinally arranged on the rack receiving area 12 substantially parallel to the rack onload edge 13. The onload rail 11 can engage with a recess 61 located at the bottom of a rack 60 such that the rack 60 can longitudinally slide on the rack receiving area 12 along the onload rail 11 when the rack 60 is engaged, the longitudinal direction is schematically by dashed arrows in FIG. 1a, which also represent the transportation path from the rack onload section 10 to the rack offload section 30. The double arrow in FIG. 1a across the rack onload edge 13 represents schematically the loading and unloading movement respectively in a direction transversal, i.e. orthogonal to the onload rail 11 at any position along the onload rail 11.

The onload section 10 can also comprise two slits 14 on either side of the onload rail 11. The onload section 10 can also comprise two push elements 15 translatable through the slits 14 via a common drive mechanism 16 located underneath the rack receiving area 12. The processing section 20 can comprise a rack processing area 22 with a processing rail 21 longitudinally arranged on the rack processing area 22. The processing section 20 can also comprise two slits 24 on either side of the processing rail 21. The processing section 20 can also comprise two push elements 25 translatable through the slits 24 via a common drive mechanism 26 located underneath the rack receiving area 22. The processing section 20 can further comprise a sample rack holding mechanism 27. The rack offload section 30 can comprise a rack offload area 32 and an offload rail 31 longitudinally arranged on the rack offload area 32 and aligned with the processing rail 21. The transfer section 40 can comprise a rack transfer area 42 substantially orthogonally arranged between the onload section 10 and the processing section 20 and a transfer element 45 substantially horizontally translatable between a position aligned with the onload rail 11 and a position aligned with the processing rail 21. The transfer section 40 can further comprise a barcode reader (not shown) for scanning barcode labels on a rack 60 and/or on the sample tubes 62 held by the rack 60 when the rack 60 is on the rack transfer area 42.

Figure 2A:
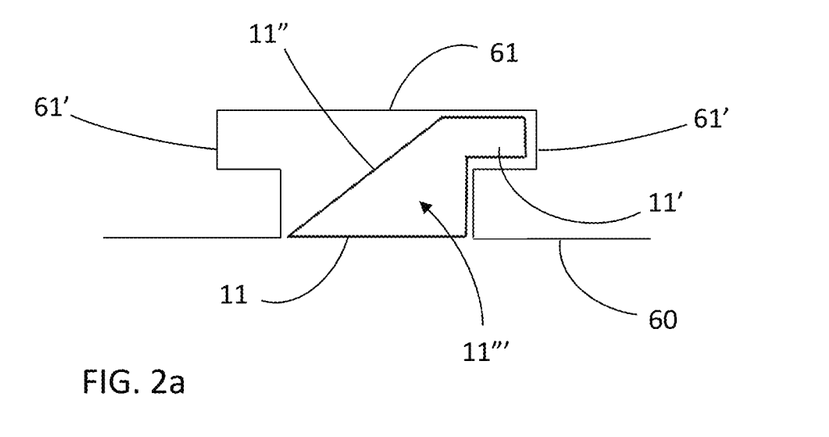
FIGS. 2a-b illustrate schematically the engagement of a rack with a rack onload rail as shown in FIGS. 1a-b compared with the engagement of the same rack with a prior art rack rail according to an embodiment of the present disclosure.
Figure 2B:
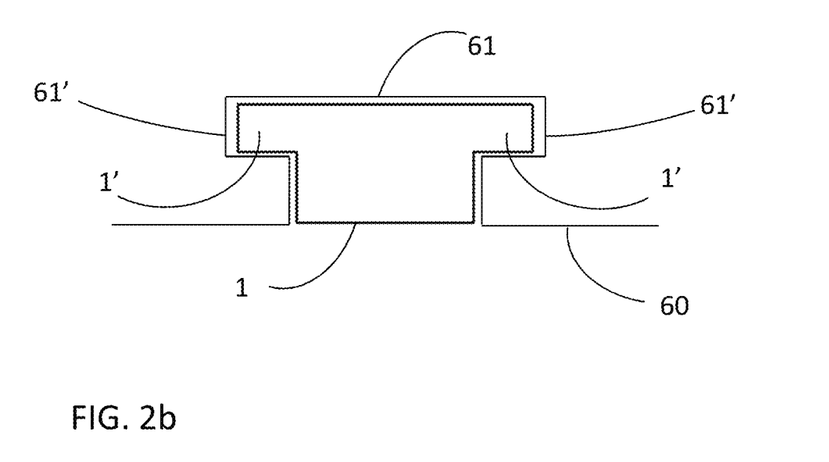

FIG. 2 shows schematically the cross-section of a rack rail such as the rack onload rail 11 compared with the cross-section of a prior art rack rail 1. In particular, FIG. 2a illustrates the engagement of a rack 60 via the recess 61 with the rack onload rail 11 and FIG. 2b illustrates the engagement of a prior art rack rail 1 with the same rack 60. The onload rail 11 can have a cross-section comprising a wedged, or substantially triangular, base portion 11''' comprising a hypotenuse, wherein the hypotenuse is an inclined onload rail side 11''. The onload rail 11 can further comprise a protrusion 11' extending from the base portion 11'''. The onload rail 11 can thus only in part form-fit, i.e. form-fit only from the side of the protrusion 11' with the recess 61 of the rack 60. In particular, the protrusion 11' can substantially fit in a recess arm 61' of the recess 61 when the rack 60 is engaged. Thus due to the form-fit part, the rack 60 can slide longitudinally along the onload rail but can be prevented from being disengaged by lifting the rack 60 vertically or by sliding the rack 60 in a direction opposite to the side of the protrusion 11' transversally to the rack onload rail 11. Due to the non-form-fit part, the rack 60 can however be disengaged by sliding the rack on the inclined onload rail side 11'' in the opposite direction. On the contrary, the rack rail 1 can comprise two protrusions 1' substantially fitting with respective recess arms 61' of the recess 61, thereby forming a form-fit engagement between the rack rail 1 and the recess 61, allowing the rack 60 only to slide longitudinally along the rack rail 1 and preventing the rack 60 from disengaging by lifting the rack 60 vertically or by sliding the rack 60 transversally to the rack rail 1.

Figures 3A, 3B, 3C:
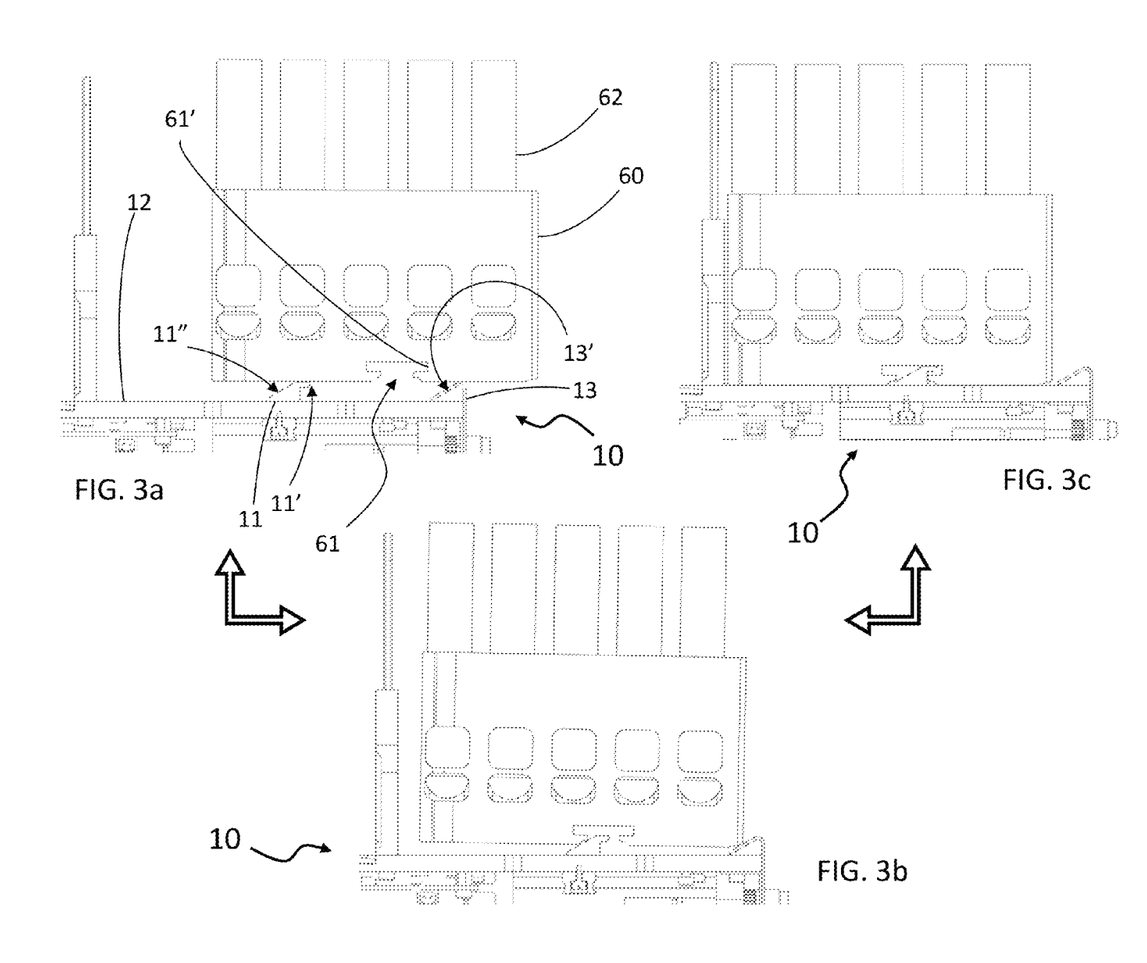
FIGS. 3a-c illustrate how a sample rack is loaded in the rack onload section or unloaded from the onload section according to an embodiment of the present disclosure.

FIG. 3 shows a cross-section of the onload section 10 and illustrates in more detail the engagement and disengagement of a rack 60 with the onload rail 11 as a rack is loaded on the rack receiving area 12 or unloaded from the onload section 10. It can be seen that the onload rail 11 can have a wedged, or substantially triangular, cross-section as shown in FIG. 2a comprising a protrusion 11' facing the rack onload edge 13 and an inclined onload rail side 11'' arranged opposite to the rack onload edge 13. The bottom side of the rack 60 can comprise a recess 61 having a width approximately equal to the width of the rack 60 and a length shorter than the length of the rack 60, and can have a substantially T shape, i.e. having a narrower lower section and a larger upper section extending with two recess arms 61' towards the shorter sides of the rack 60 respectively. The recess 61 can be in a position different from the center of the rack 60, i.e. closer to one shorter side. The onload rail 11 can also longitudinally be at a position different from the center of the rack receiving area 12, and spaced from the onload edge 13 of a distance which can be substantially equivalent to the distance of the recess 61 from one short side of the rack 60. This can make sure that the rack 60 can be loaded only in one orientation so to enable, for example, the reading of the barcodes from the right side or to correctly identify each sample tube 62, if for example the rack 60 can be identified rather than each individual tube 62. The protrusion 11' and the inclined rail side 11'' can be arranged such that the recess 61, in particular one recess arm 61', of a rack 60 can engage with the protrusion 11" when the rack 60 is loaded on the rack receiving area 12 transversally from the rack onload edge 13 and the recess 61 can disengages from the onload rail 11 by sliding the rack transversally on the inclined onload rail side 11" in the direction of the rack onload edge 13. The rack onload edge 13 can comprise an inclined onload edge side 13' facing the onload rail 11 and substantially parallel to the inclined onload rail side 11" such that the recess 61 can engage with the onload rail 11 and can disengage from the onload rail 11 by sliding the rack transversally on the inclined onload rail side 11" and the inclined onload edge side 13' in opposite directions respectively. The onload rail 11 and the onload edge 13 can have the same height so that the bottom of the rack may be laid substantially horizontal as a bridge on top of the onload rail 11 and onload edge 13 (FIG. 3a). As the distance between the onload edge 13 and the onload rail 11 can be substantially equivalent to the distance between the recess 61 and one shorter side of the rack 60, by sliding the rack 60 in one orientation from the onload edge 13 towards the onload rail 11 the bottom of the rack can be gradually lowered (FIG. 3b) until the recess 61, specifically one recess arm 61' is engaged with the protrusion 11' of the onload rail 11 and the bottom of the rack 60 can lay flat on the rack receiving area 12 (FIG. 3c). Analogously, by sliding the rack 60 in the opposite direction towards the onload edge 13 the rack can be gradually raised (FIG. 2b) until the recess disengages and the bottom of the rack 60 lays flat on top of the onload rail 11 and onload edge 13 (FIG. 3a).

Figure 4A:
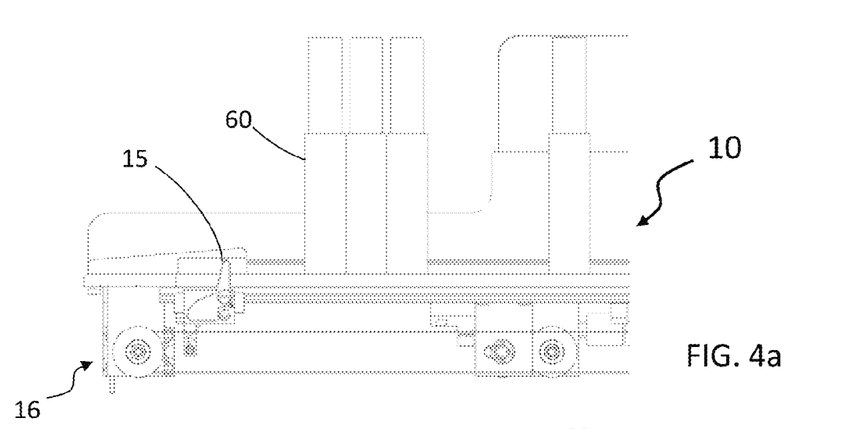
FIGS. 4a-d illustrate the mechanism of a push element according to an embodiment of the present disclosure.
Figures 4B, 4C, 4D:
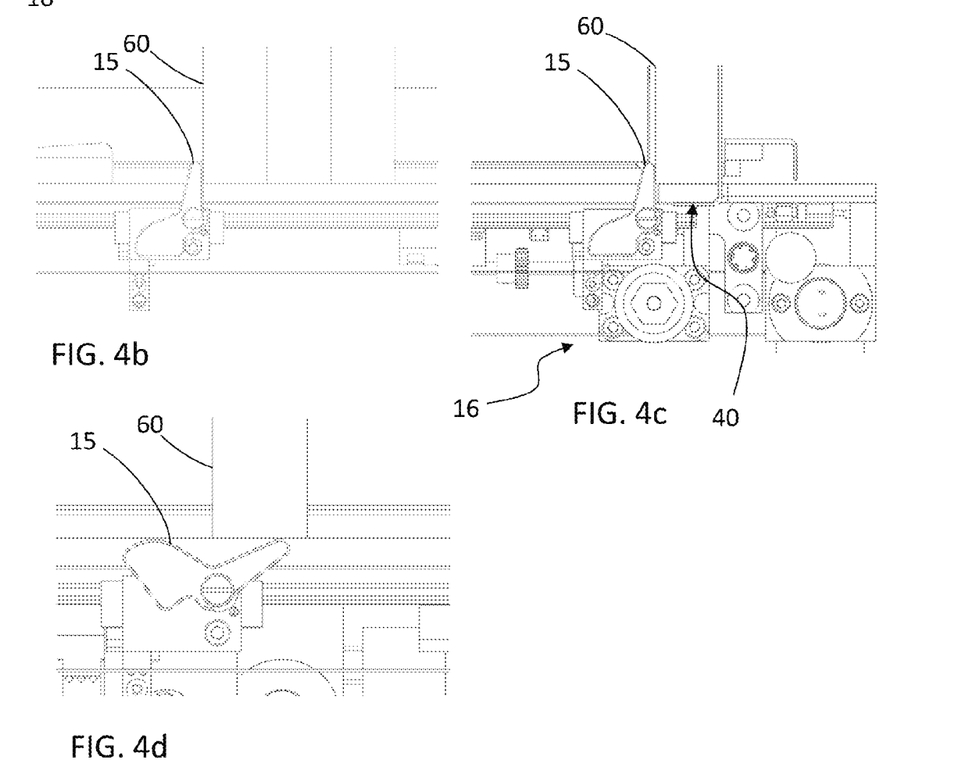

FIG. 4 depicts the mechanism of a push element 15 of the onload section 10. The onload push element 15 can push in the direction of the transfer section 40 and can retract in the opposite direction, for example to return to a previous position or to a home position before pushing again, for example for re-compacting a plurality of racks 60 spread on the rack receiving area 12 along the onload rail 11, for example after leaving a gap between racks 60 due for example to the transversally unloading of a rack 60. FIG. 4a shows the onload push element 15 in the home position. FIG. 4b shows the onload push element 15 in a pushing position against the long side of a rack 60. FIG. 4c shows the onload pushing element 15 in its most forward position in which a rack 60 has been pushed out of the rack receiving area 12 onto the rack transfer area 42. FIG. 4d shows the onload push element 15 in a retracted position under a rack 60 during a backwards translation. The push element 15 can be pivotally retractable by a resilient member (not shown) and can be translatable through the slit 14 by a drive mechanism 16 under the rack receiving area 12.

Figure 5A:
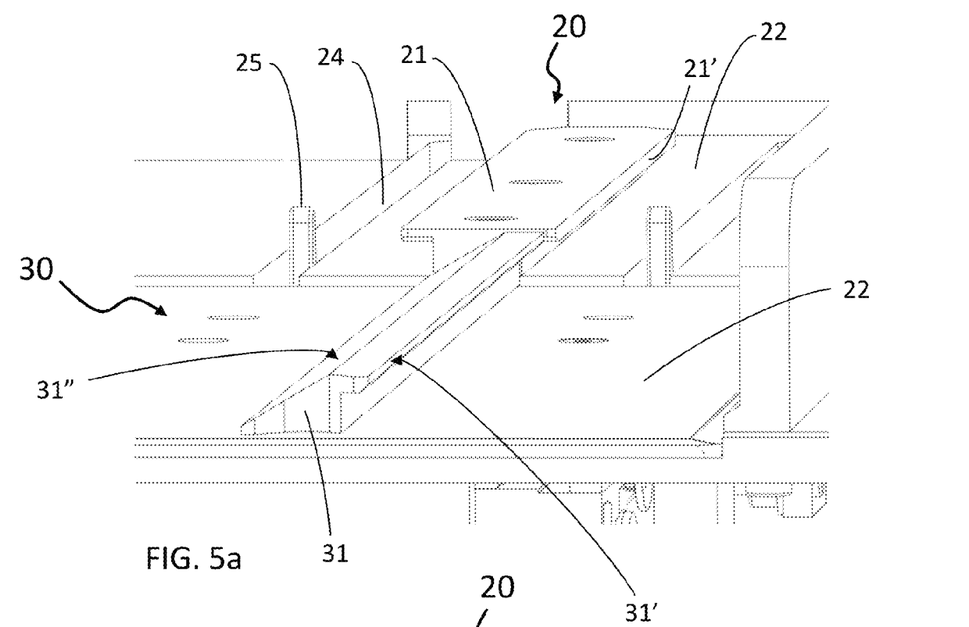
FIGS. 5a-b illustrate the arrangement of the rack offload section with respect to the sample processing section in perspective according to an embodiment of the present disclosure.
Figure 5B:
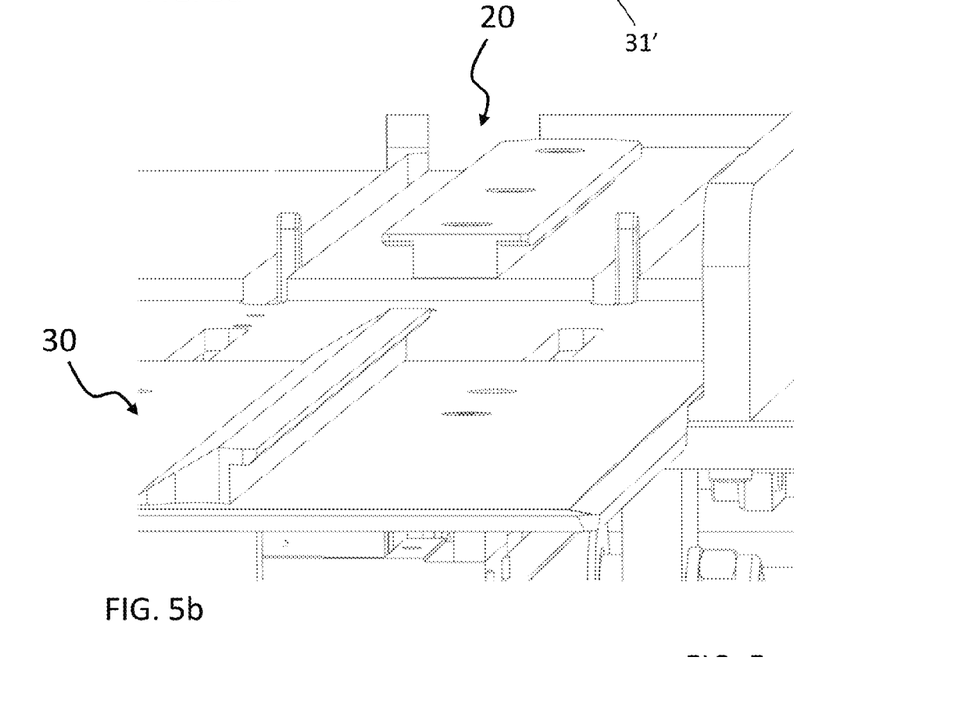

FIG. 5 shows the arrangement of the rack offload section 30 with respect to the sample processing section 20 in perspective. Also the processing rail 21 and offload rail 31 are shown in more detail. The processing rail 21 can have a substantially symmetric T-shaped cross-section with two protrusions 21' similar to that shown in FIG. 2b such that the recess 61 of a rack 60 can engage and disengage only by sliding the rack 60 on the rack processing area 22 longitudinally along the processing rail 21, i.e. engaged at one extremity of the processing rail 21 and disengaged at the other extremity of the processing rail 21 after sliding along the length of the processing rail 21 in the direction of the offload section 30. A rack 60 can therefore be prevented from disengaging transversally or in the upward direction from the processing rail 21 and can also be prevented from rising with the bottom from the rack processing area 22. Analogously to the onload push element of FIG. 4, the processing push elements 25 can push only in one direction, in this case in the direction of the rack offload section 30 and to pivotally retract when translated in the opposite direction if one or more racks 60 are encountered on the rack processing area 22.

The offload rail 31 can have a wedged, or substantially triangular, cross-section similar to that of the onload rail 11. The offload rail 31 can comprise a protrusion 31' and an inclined offload rail side 31" arranged such that the recess 61 can disengage from the offload rail 31 by sliding the rack 60 transversally on the inclined offload rail side 31" or by sliding the rack 60 longitudinally along the offload rail 31. The sample processing section 20 and the rack offload section 30 can be arranged such that the processing rail 21 and the offload rail 31 can be aligned with each other such that the racks can slide from the processing rail 21 to the offload rail 31, in this case by the action of the processing push elements 25. Both the processing rail 21 and the offload rail 31 can be arranged on the rack processing area 22 and the rack offload area 32 respectively such that the rack can engage in just one orientation analogously to the onload rail 11 on the rack receiving section 12. Also, the rack offload section 30 can be a drawer translatable between two positions, one position closely adjacent to the sample processing section such as to enable the transfer of racks 60 from the sample processing section 20 to the rack offload section 30 (FIG. 5a) and one position where the rack offload section 30 can be longitudinally separated from the sample processing section 20 such as to enable easier access to the racks on the rack offload area 30 (FIG. 5b).

Figure 6A:
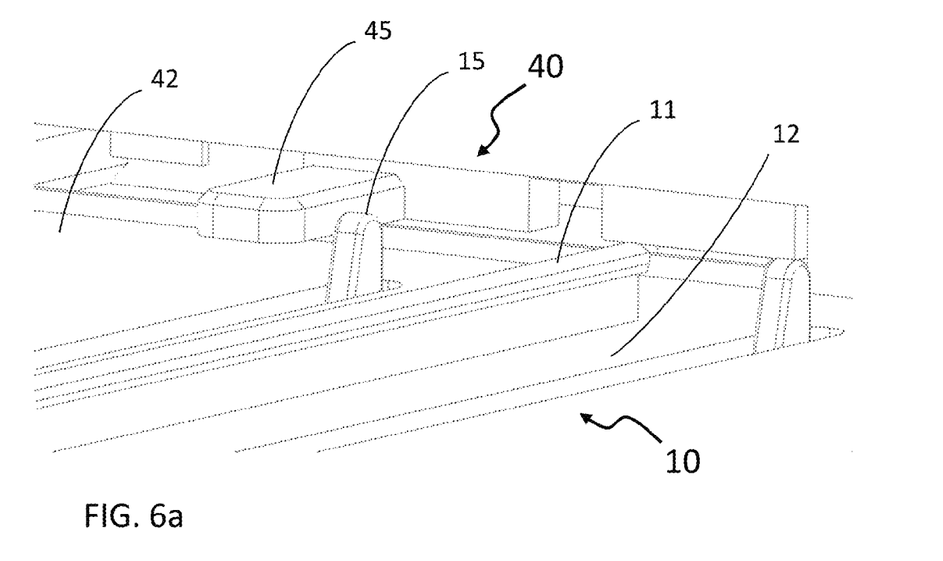
FIGS. 6a-b illustrate the mechanism of the rack transfer section according to an embodiment of the present disclosure.
Figure 6B:
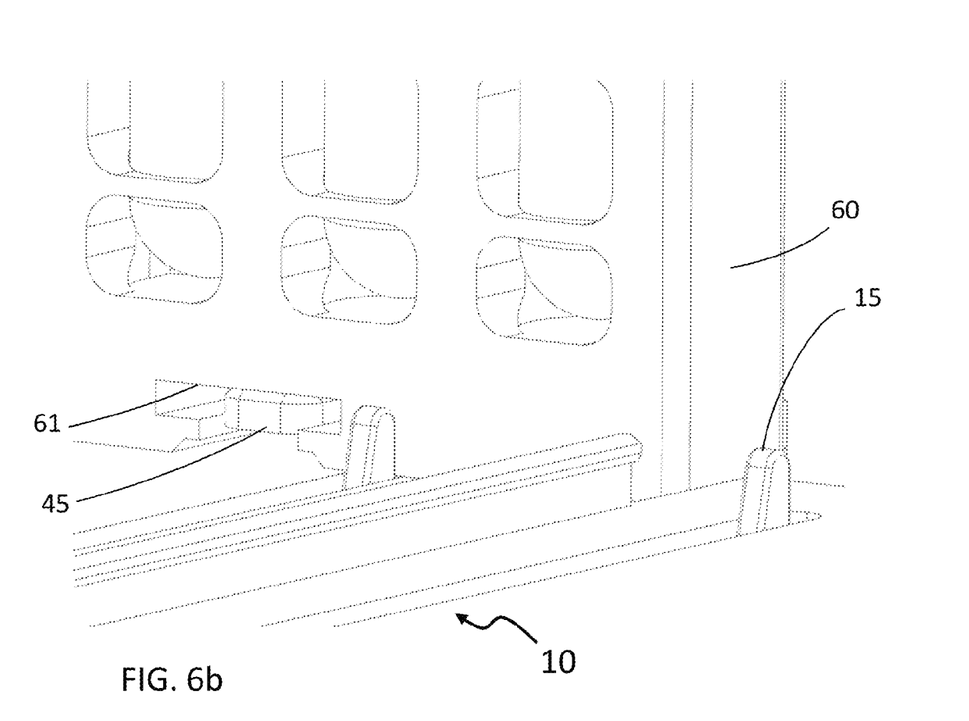

FIG. 6 shows in perspective the engagement of the transfer element 45 with a rack 60 on the rack transfer area 42. FIG. 6a shows a disengaged transfer element 45 and FIG. 6b shows the transfer element 45 engaged with a rack 60. The transfer element 45 can be a substantially horizontal bar to substantially fit in the recess 61 of the rack 60. The onload push elements 15 and the transfer element 45 can cooperate such as the recess 61 can disengage from the onload rail 11 and can engage with the transfer element 45 when it is aligned with the onload rail 11 as shown in FIG. 1a. The transfer element 45 can then push the rack 60 on the transfer area 42 (FIG. 6b) until the transfer element 45 and the recess 61 are aligned with the processing rail 21 of the sample processing section 20 (not shown). The processing push elements 25 can then push the rack 60 onto the rack processing area 22 such as the recess 61 engage with the processing rail 21.

Figure 7A:
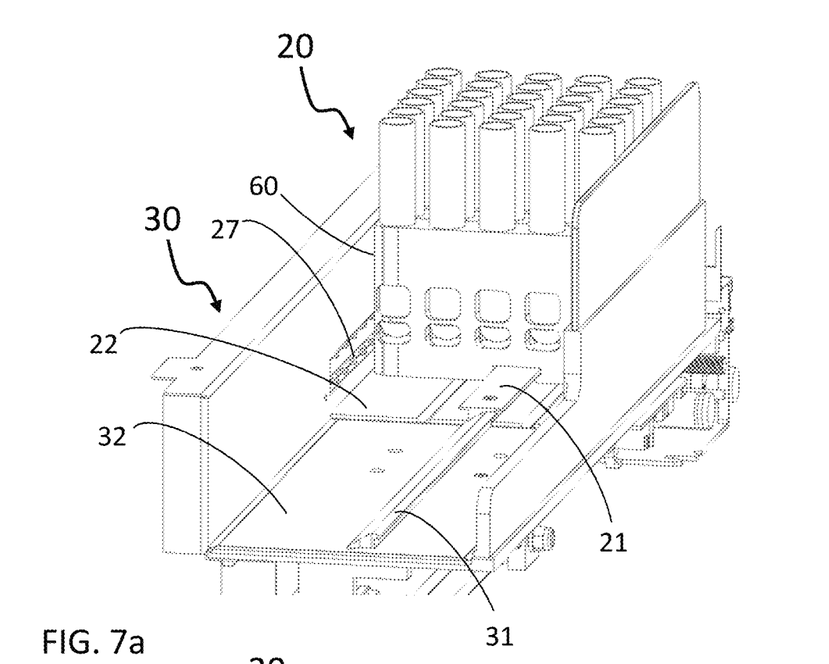
FIGS. 7a-b illustrates an example of rack holding mechanism according to an embodiment of the present disclosure.
Figure 7B:
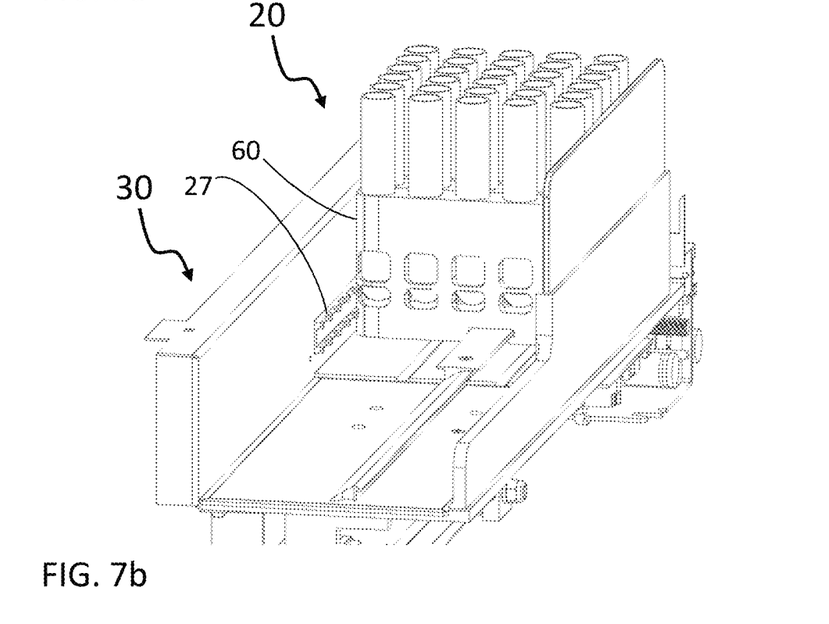

FIG. 7 depicts an example of rack holding mechanism 27 in the sample processing section 20. The rack holding mechanism 27 can move between an open position (FIG. 7a) and a holding position (FIG. 7b), wherein in the holding position the rack holding mechanism 27 can prevent one or more racks from moving longitudinally along the processing rail 21 and in the open position racks 60 can move longitudinally along the processing rail 21, for example by the action of the processing push elements 25. The holding mechanism 27 can be a ridge at one edge of the rack processing area 22 substantially parallel to the processing rail 21, which in the open position can be retracted and in the holding position can be advanced such as to become in contact with one or more racks on the rack processing area 22. The holding mechanism 27 can have a front comb-like shape comprising a plurality of protruding teeth that embrace a respective number of beveled shorter sides of a plurality of racks 60 when the rack holding mechanism 27 is in the holding position.

Figure 8A:
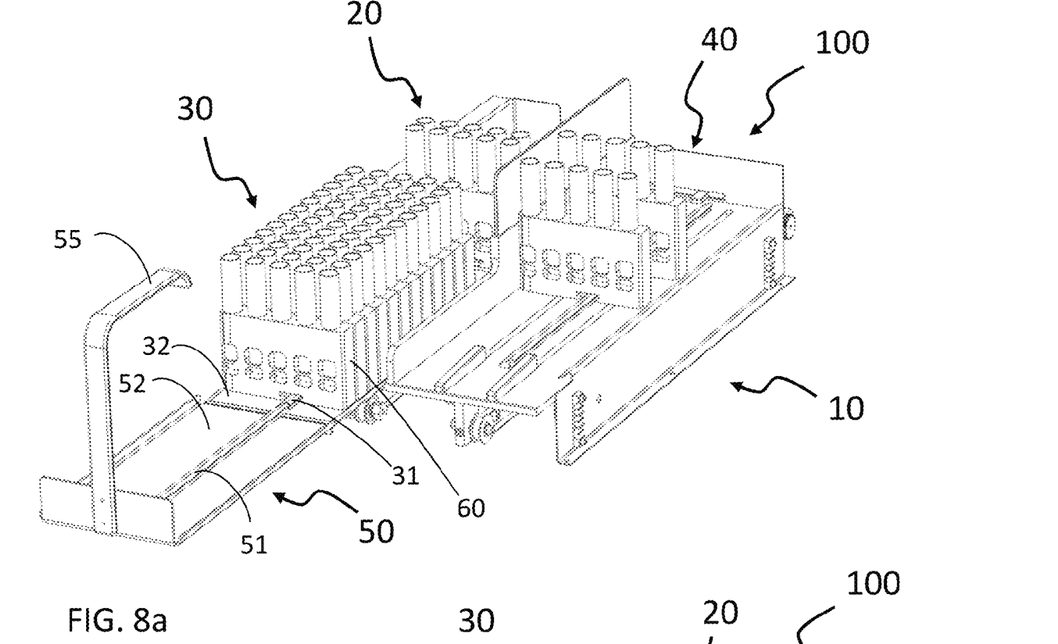
FIGS. 8a-b illustrate the sample rack handling unit of FIGS. 1a-b comprising a rack offload tray according to an embodiment of the present disclosure.
Figure 8B:
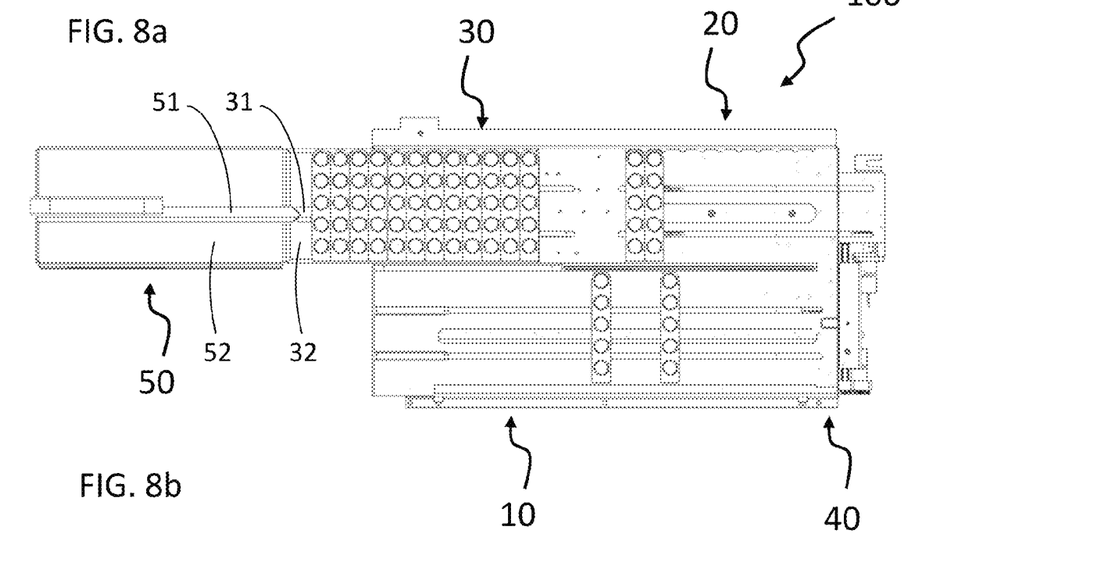

FIG. 8 shows the sample rack handling unit 100 of FIG. 1 comprising a rack offload tray 50 and a plurality of racks 60 in the rack onload section 10, in the sample processing section 20 and in the rack offload section 30 respectively. FIG. 8a is a perspective view and FIG. 8b is a top view. The rack offload section 30 can be a full of racks 60, which can have been pushed one by one onto the rack offload area 32 from the rack processing area 22 after the samples contained therein have been processed in the sample processing section 20. The rack offload section 30 is shown in the translated position, i.e. longitudinally separated from the sample processing section 20 for easier access from the outside to the racks 60 on the rack offload area 32. The offload tray 50 can comprise a transportation handle 55 for being hand held and can receive racks 60 from the rack offload area 32. The rack offload tray 50 can comprise a rack tray area 52 and a tray rail 51 on the rack tray area 52 that can be aligned with the rack offload area 32 and the offload rail 31 of the rack offload section 30 respectively. In this example, the tray rail 51 can extend longitudinally slightly out of the rack tray area 52 and can end with a shape which is complementary to the end of the offload rail 31. The offload rail 31 can terminate slightly before the end of the rack offload area 32 and can leave a gap corresponding to the length of the tray rail 51 protruding from the rack tray area 52. In this way, it can be easier to achieve alignment of the rack offload tray 50 with the rack offload section 30 as shown in FIG. 8 and to maintain alignment while racks 60 are being transferred. Such alignment can enable one or more racks 60, for example, all the racks 60 on the rack offload area 32 to be transferred from the rack offload area 32 to the rack tray area 52 by sliding the racks 60, for example, by pushing all the stacks of racks from behind, along the offload rail 31 in direction of the tray rail 51 so that the racks 60 can disengage one by one from the offload rail 31 and can engage with the tray rail 51.

Figure 9A:
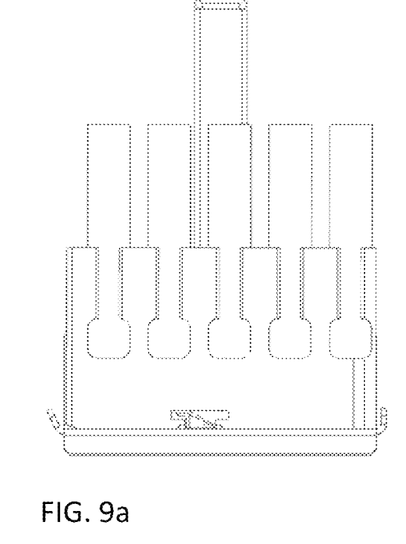
FIGS. 9a-c illustrate an offload tray more in detail according to an embodiment of the present disclosure.
Figure 9B:
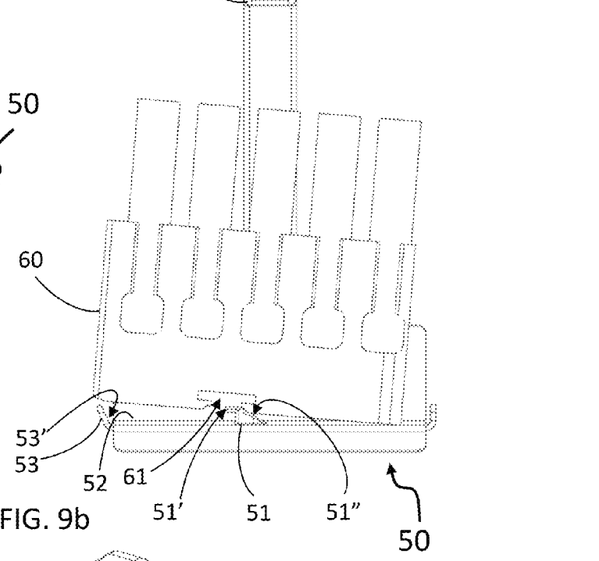
Figure 9C:
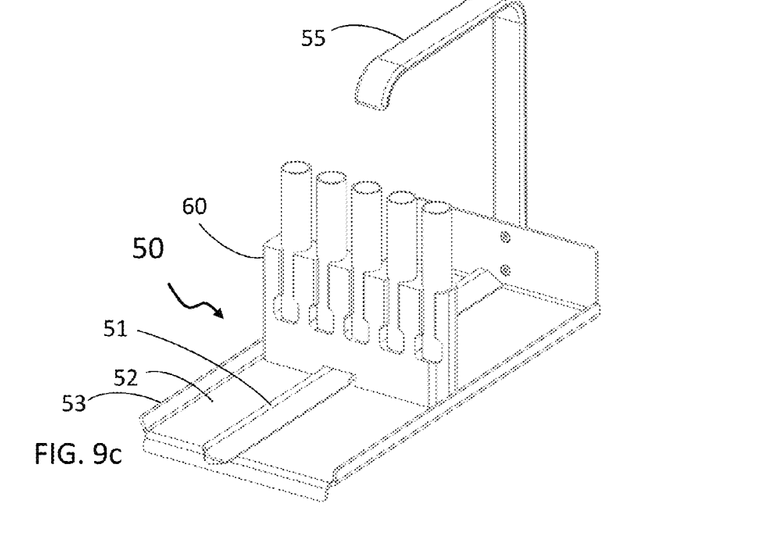

FIG. 9 shows the offload tray 50 more in detail. In particular, FIG. 9a shows the offload tray 50 with a rack 60 engaged with the tray rail 51. FIG. 9b shows how the rack 60 can be unloaded from the offload tray 50. FIG. 9c shows the offload tray 50 in perspective. The tray rail 51 can have a wedged, or substantially triangular, cross-section similar to that of the offload rail 31 and onload rail 11. The tray rail 51 can comprise a protrusion 51' and an inclined tray rail side 51" arranged such that the recess 61 of the rack 60 can disengage from the tray rail 51 by sliding the rack 60 transversally on the inclined offload rail side 51". Alternatively, the rack 60, or a plurality of racks 60, may be unloaded from the offload trail 50 by sliding the racks 60 longitudinally along the tray rail 51. FIG. 9 shows also the transportation handle 55 and a rack tray offload edge 53 comprising an inclined offload edge side 53' similar to the inclined onload edge side 13' of the rack onload section 10.

Figure 10:
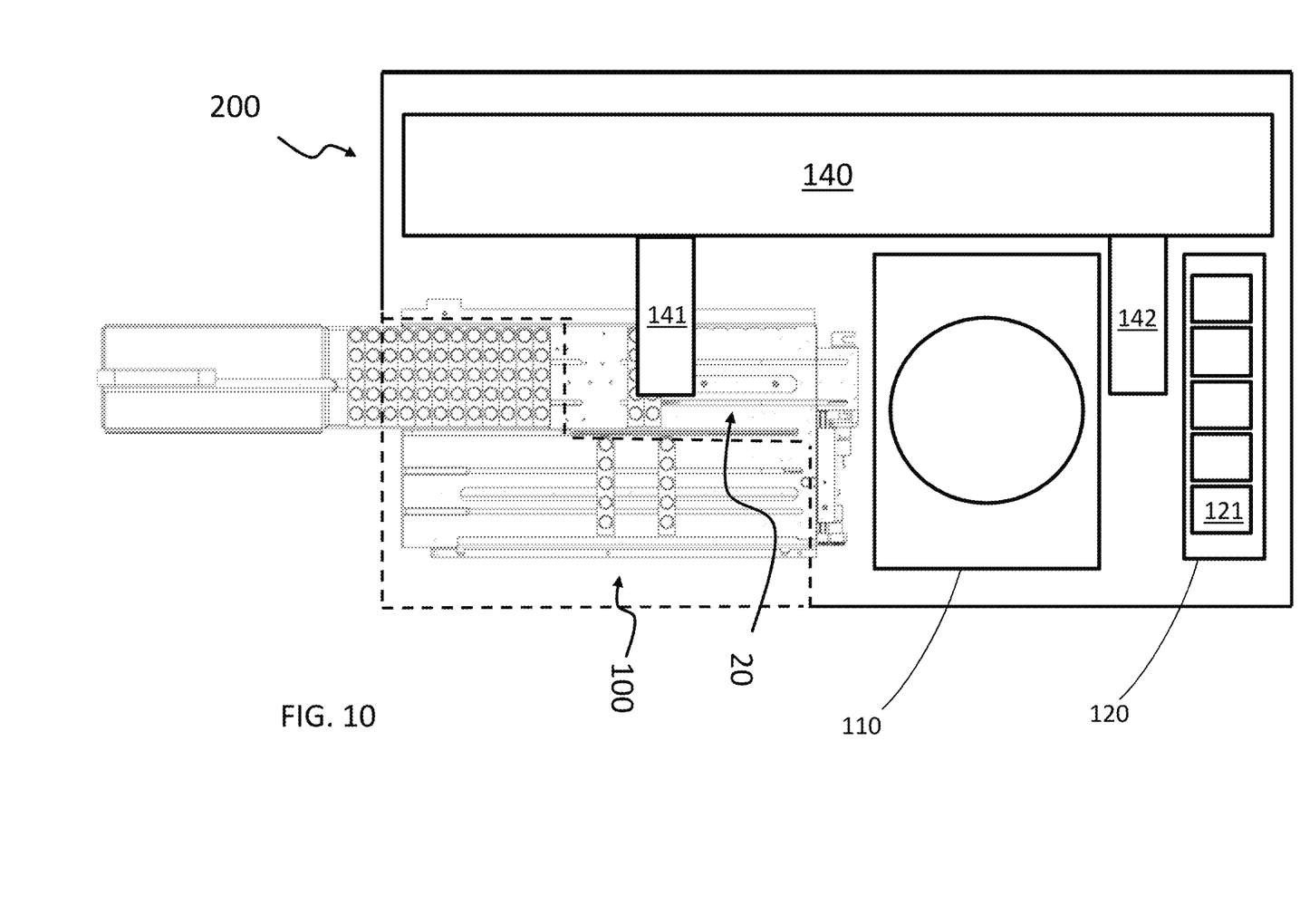
FIG. 10 illustrates schematically an analytical instrument comprising the sample rack handling unit of FIGS. 8a-b according to an embodiment of the present disclosure.

FIG. 10 shows schematically an example of analytical instrument 200 for the in vitro diagnostic analysis of biological samples comprising the sample rack handling unit 100 of FIG. 8b. The dashed line indicates the area of the instrument 200, particularly of the sample rack handling unit 100, which can be accessible from the outside of the instrument 200 for loading and/or unloading sample racks 60. The analytical instrument 200 can also comprise an analytical unit 110, such as a clinical chemistry or coagulation analyzer, for analyzing at least one sample from the sample tubes 62 held in the at least one sample rack 60. The analytical instrument 200 can also comprise a reagent holding unit 120 for holding reagents to perform the assays. Reagents can be in the form of containers or cassettes 121 containing individual reagents or group of reagents. The analytical instrument 200 can comprise a liquid processing unit 140, comprising a first pipetting unit 141 to pipette samples from the sample tubes 62 on the sample processing section 20, and particularly when the holding mechanism 27 is in the holding position. The liquid processing unit 140 can comprise also a second pipetting unit 142 to pipette reagents from the reagent holding unit 120. Samples and reagents can then be mixed and analyzed in the analyzer 110. The analytical instrument 200 may comprise other units.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A sample rack handling unit, the sampling rack handling unit comprising:
   a rack onload section for loading one or more sample racks that hold a sample container, the rack onload section comprising,
      a rack onload edge having an inclined side, and
      a rack receiving area with an onload rail longitudinally arranged on the rack receiving area parallel to the rack onload edge, the onload rail engages a recess located at the bottom of a rack such that the rack longitudinally slides on the rack receiving area along the onload rail when the rack is engaged,
   wherein the onload rail has a cross-section comprising a triangular shaped base portion having a hypotenuse, wherein the hypotenuse of the triangular shaped base portion comprises an inclined onload rail side opposite to the rack onload edge, and a protrusion extending from an upper corner of the hypotenuse of the triangular shaped base portion, wherein the protrusion extends outwards towards the rack onload edge, such that the recess engages the onload rail when the rack is loaded on the rack receiving area from the rack onload edge transversely to the onload rail and the recess disengages from the onload rail by sliding the rack in the direction of the rack onload edge.

2. The sample rack handling unit according to claim 1, wherein the inclined side faces the onload rail and is arranged substantially parallel to the inclined onload rail side such that the recess engages the onload rail and disengages from the onload rail by sliding the rack transversally on the inclined onload rail side and the inclined side in opposite directions respectively.

3. The sample rack handling unit according to claim 1, further comprising,
   a sample processing section parallel and adjacent to the rack onload section to receive racks from the rack onload section and to enable processing of samples from sample containers contained in the racks, the sample processing section comprising a processing rail, the processing rail engages the recess such that the rack is longitudinally slides along the processing rail when the rack is engaged.

4. The sample rack handling unit according to claim 3, wherein the processing rail has a cross-section which form-fits with the recess such that the recess engages and disengages only by sliding longitudinally along the processing rail.

5. The sample rack handling unit according to claim 3, wherein the sample processing section comprises a rack holding mechanism comprising a ridge located parallel to the processing rail movable between an open position, where the ridge is retracted, and a holding position, where the ridge is advanced and contacts one or more racks, wherein in the holding position, the rack holding mechanism prevents one or more racks to move longitudinally along the processing rail.

6. The sample rack handling unit according to claim 5, wherein the sample processing section comprises a pipetting unit to pipette a sample from a sample container when the holding mechanism is in the holding position.

7. The sample rack handling unit according to claim 3, further comprising,
a sample rack offload section parallel and adjacent to the rack onload section and connected to the sample processing section to unload racks received from the sample processing section wherein the rack offload section comprises an offload rack area and an offload rail on the offload rack area, wherein the offload rail comprising a protrusion and an inclined offload rail side arranged such that the recess disengages from the offload rail by sliding the rack transversally on the inclined offload rail side or by sliding the rack longitudinally along the offload rail.

8. The sample rack handling unit according to claim 7, wherein the offload rail has a substantially triangular cross-section.

9. The sample rack handling unit according to claim 7, wherein the sample rack offload section is translatable and/or removable from the sample rack handling unit.

10. The sample rack handling unit according to claim 7, wherein the sample rack offload section comprises a separate rack offload tray to receive racks from the rack offload area comprising a handle for being hand held, a rack tray area and a tray rail on the rack tray area aligned with the offload rail wherein the tray rail has a wedged, or substantially triangular, cross-section comprising a protrusion and an inclined tray rail side arranged such that the recess is disengages from the tray rail by sliding the rack transversally on the inclined offload rail side or by sliding the rack longitudinally along the tray rail.

11. The sample rack handling unit according to claim 7, wherein the rack onload section, the sample processing section and the rack offload section are arranged such that at least two rack rails chosen from the group of the onload rail, the processing rail and the offload rail are aligned with each other such that the racks slide between the rack rails.

12. The sample rack handling unit according to claim 3, further comprising,
at least one push or pull element translatable in a direction parallel to a rack rail chosen from the group of the onload rail and the processing rail such as to push or pull one or more sample racks engaged with the onload rail and/or with the processing rail longitudinally along the onload rail and/or processing rail.

13. The sample rack handling unit according to claim 12, wherein the at least one push or pull element pushes or pulls only in one direction and is retractable when translated in the opposite direction.

14. The sample rack handling unit according to claim 3, further comprising,
a sample rack transfer section located between the rack onload section and the sample processing section, the sample rack transfer section comprising a transfer element to transfer at least one rack at a time from the rack onload section to the sample processing section.

* * * * *